United States Patent [19]

Anderson

[11] Patent Number: 4,517,193
[45] Date of Patent: May 14, 1985

[54] PESTICIDAL BENZOYLUREA COMPOUNDS

[75] Inventor: Martin Anderson, Whitstable, England

[73] Assignee: Shell Oil Company, Houston, Tex.

[21] Appl. No.: 529,909

[22] Filed: Sep. 7, 1983

[30] Foreign Application Priority Data

Sep. 16, 1982 [GB] United Kingdom ............... 8226386

[51] Int. Cl.³ ................... C07C 145/04; A01N 47/34
[52] U.S. Cl. .................................. 514/471; 514/522; 514/535; 260/465 D; 260/501.16; 260/501.21; 546/288; 546/297; 546/300; 549/496; 560/13; 560/18; 562/430; 562/432
[58] Field of Search ............ 560/13, 18; 260/453 RW, 260/465 D, 453 R, 501.16, 501.21; 546/288, 300, 297; 549/496; 562/430, 432; 424/285, 263, 304, 309, 316, 319

[56] References Cited

U.S. PATENT DOCUMENTS 4,005,223  1/1977  Sirrenberg et al. ............... 424/322
4,139,636  2/1979  Sirrenberg et al. ............... 424/322

Primary Examiner—Michael L. Shippen

[57] ABSTRACT

A benzoylurea compound of formula:

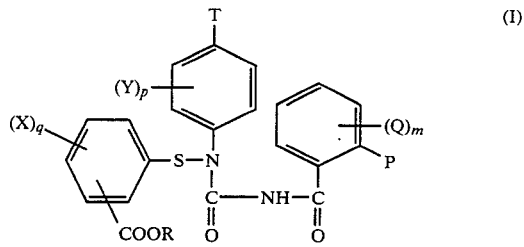

in which each of P and Q independently represents a halogen atom or an alkyl group; m represents 0, 1 or 2; R represents an optionally-substituted alkyl, alkenyl, alkynyl, cycloalkyl or phenyl group, a hydrogen atom, one equivalent of an alkali metal or alkaline earth metal, or an ammonium or substituted ammonium group; each X independently represents a halogen atom, a cyano, nitro or carboxy group, or an optionally-substituted alkyl, alkoxy, alkylthio, cycloalkyl, cycloalkyloxy, cycloalkylthio, alkenyl, alkenylthio, alkylcarbonyl, alkoxycarbonyl, alkylsulphonyl, alkynyl, phenyl, phenoxy, phenylthio or amino group; $q=0$, 1, 2, 3 or 4; T represents a halogen atom, an alkyl, haloalkyl, alkoxy, haloalkoxy, alkenyloxy or haloalkenyloxy group, or a phenoxy or pyridyloxy group optionally substituted by one or more substituents selected from halogen atoms and nitro, alkyl, haloalkyl and cyano groups; each Y independently represents a halogen atom or a nitro, cyano, alkyl or haloalkyl group; and $p=0$, 1, 2, 3 or 4. The compounds have pesticidal activity, and may be prepared from novel sulphenamide starting materials.

4 Claims, No Drawings

PESTICIDAL BENZOYLUREA COMPOUNDS

The present invention relates to benzoylurea compounds and their preparation, to compositions containing such compounds, and to their use as pesticides.

GB Nos. 1,460,410 and 1,501,607 disclose that certain disubstituted ureas have pesticidal activity.

The Applicants have now discovered that a further class of novel urea derivatives have pesticidal activity. These ureas are trisubstituted, and contain a specifically-substituted phenylthio group.

Accordingly, the present invention provides a benzoylurea compound of formula:

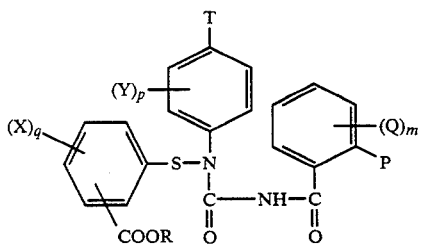

in which each of P and Q independently represents a halogen atom or an alkyl group; m represents 0, 1 or 2; R represents an optionally-substituted alkyl, alkenyl, alkynyl, cycloalkyl or phenyl group, a hydrogen atom, one equivalent of an alkali metal or alkaline earth metal, or an ammonium or substituted ammonium group; each X independently represents a halogen atom, a cyano, nitro or carboxy group, or an optionally-substituted alkyl, alkoxy, alkylthio, cycloalkyl, cycloalkyloxy, cycloalkylthio, alkenyl, alkenylthio, alkylcarbonyl, alkoxycarbonyl, alkylsulphonyl, alkynyl, phenyl, phenoxy, phenylthio or amino group; q=0, 1, 2, 3 or 4; T represents a halogen atom, an alkyl, haloalkyl, alkoxy, haloalkoxy, alkenyloxy or haloalkenyloxy group, or a phenoxy or pyridyloxy group optionally substituted by one or more substituents selected from halogen atoms and nitro, alkyl, haloalkyl and cyano groups; each Y independently represents a halogen atom or a nitro, cyano, alkyl or haloalkyl group; and p=0, 1, 2, 3 or 4.

Except where otherwise stated, throughout this Specification and claims, alkyl, alkenyl and alkynyl moieties preferably have up to 6, especially up to 4, carbon atoms, and cycloalkyl groups preferably have 3 to 7 ring carbon atoms. Halogen atoms may be iodine, bromine, chlorine or fluorine atoms, with fluorine and chlorine atoms being preferred. A heterocyclyl group preferably contains one oxygen, sulphur or nitrogen atom, may be saturated or unsaturated, and preferably has 5 or 6 atoms in the ring.

Optional substituents which may be present in an optionally substituted alkyl, alkenyl or alkynyl moiety include halogen atoms, alkoxy, haloalkoxy, hydroxy, carboxy, alkoxycarbonyl, cycloalkyl, and heterocyclyl groups, groups of formula —O—$(CH_2CH_2O)_n$alkyl where n is 1 to 4, and optionally substituted phenyl groups. These substituents may also be present in optionally substituted cycloalkyl groups, along with alkyl and haloalkyl groups. Optional substituents which may be present in optionally substituted phenyl, phenoxy and pyridyloxy groups include halogen atoms and alkyl, haloalkyl, alkoxy, haloalkoxy, alkenyl, haloalkenyl, nitro and cyano groups.

Preferably each of P and Q independently represents a C(1–4)alkyl, especially methyl, group, or a fluorine, chlorine or bromine atom, and m is 0 or 1. If m is 1, Q is preferably in the 6 position of the phenyl ring.

Preferably T represents a bromine or, especially, fluorine or chlorine atom; a C(1–4)alkyl, haloalkyl or haloalkoxy group, especially a methyl, trifluoromethyl or trifluoromethoxy group; an optionally substituted phenoxy group in which the optional substituents are selected from C(1–4)alkyl and haloalkyl, especially methyl and trifluoromethyl, groups, fluorine and chlorine atoms, and nitro and cyano groups; or an optionally substituted pyridyloxy group in which the optional substituents are selected from trifluoromethyl groups and fluorine and chlorine atoms.

When T contains a pyridyloxy group, the pyridyl moiety is preferably a 2-pyridyl moiety; if this 2-pyridyl moiety is substituted, it preferably bears halogen or haloalkyl, especially trifluoromethyl, substituents, preferably in the 3-, 5- or 3,5-positions.

When T is a trifluoromethylphenoxy group this is preferably a 4-trifluoromethylphenoxy group and, when the phenoxy moiety thereof is further substituted, this substitution is preferably in the 2-position. Thus 2-chloro-4-trifluoromethylphenoxy, 2-fluoro-4-trifluoromethylphenoxy and 2-cyano-4-trifluoromethylphenoxy are preferred examples of the group T.

Preferably p=1 when T is a 4-substituted phenoxy group, or p=0 when T is a 4-substituted-phenoxy group bearing a second substituent.

Preferably Y represents a fluorine, chlorine or bromine atom, a C(1–4)alkyl or haloalkyl group, or a nitro or cyano group. Preferably p is 0, 1 or 2.

Preferably X represents a bromine or, especially, chlorine or fluorine atom, or a C(1–4)alkyl group. Preferably q is 0 or 1, especially 0.

Preferably R represents an optionally substituted alkyl group containing 1 to 20, especially 1 to 15, carbon atoms, a C(3–6)cycloalkyl group, or an optionally substituted phenyl group. Preferred substituents in an optionally substituted phenyl group R are selected from C(1–4)alkyl and haloalkyl groups, such as methyl and trifluoromethyl groups, nitro and cyano groups, and halogen atoms, especially fluorine and chlorine atoms.

Preferred substituents in an optionally substituted alkyl group R are halogen atoms, especially chlorine and fluorine atoms; C(1–4)alkoxy groups, especially methoxy and ethoxy groups; carboxy groups; alkoxycarbonyl groups containing 2 to 5 carbon atoms, for example ethoxycarbonyl and methoxycarbonyl groups; groups of formula —O—$(CH_2CH_2O)_n$ alkyl where n is 1 to 4, especially 1, and the alkyl moiety has 1 to 4, especially 1 or 2, carbon atoms; optionally substituted phenyl groups in which the preferred optional substituents are as given above for an optionally substituted phenyl group R; and heterocyclic groups, especially tetrahydrofuryl groups.

In one preferred embodiment of the invention, R represents an unsubstituted alkyl group having 1 to 20 carbon atoms, especially 1 to 10 carbon atoms, most preferably 1 to 5 carbon atoms.

In a further preferred embodiment of the invention, R represents a group of general formula $$-(CH_2CH_2O)_nR^1 \qquad (II)$$

in which $R^1$ represents an optionally-substituted alkyl, alkenyl, alkynyl, cycloalkyl or phenyl group, and n represents 1, 2, 3, 4 or 5. Preferably R¹ represents an alkyl or haloalkyl group containing 1 to 10 carbon atoms, the halogen being chlorine or fluorine. Most preferably, R¹ represents an alkyl group having 1 to 4 carbon atoms, for example methyl, ethyl, isopropyl or tertiary butyl. Preferably n is 1 or 2. Preferably the group —COO(CH₂CH₂O)$_n$R¹ is located on the 2-position of the phenyl ring of the phenylthio group.

Thus typical benzoylureas according to the invention have the general formula I in which each of P and Q independently represents a fluorine, chlorine or bromine atom or an alkyl group containing 1 to 4 carbon atoms and m represents 0 or 1; R represents an alkyl, haloalkyl or alkoxyalkyl group containing 1 to 15, especially 1 to 10, carbon atoms and in which the halogen substituent is chlorine or fluorine and the alkoxy substituent contains 1 to 4 carbon atoms; one equivalent of an alkali metal or alkaline earth metal; or an ammonium or a C(1–6)alkyl-substituted-ammonium group; each X represents a fluorine, chlorine or bromine atom, or an alkyl group of 1 to 4 carbon atoms and q=0, 1, 2, 3 or 4; T represents a fluorine, chlorine or bromine atom, a haloalkyl or haloalkoxy group of 1 to 4 carbon atoms in which the halogen substituent is fluorine, chlorine and/or bromine, or a trihalomethyl-, nitro-, or cyanophenoxy group in which the phenoxy moiety can also bear one or more fluorine, chlorine or bromine, C(1–4)alkyl, nitro or cyano substituents; each Y independently represents a fluorine, chlorine, or bromine atom, a nitro or cyano group, or a C(1–4)alkyl or haloalkyl group in which the halogen substituent is fluorine, chlorine or bromine; and p=0, 1, 2, 3 or 4.

More preferred benzoylureas according to the invention have the general formula I in which each of P and Q independently represents a fluorine, chlorine or bromine atom; m represents 0 or 1; R represents a C(1–10)alkyl or haloalkyl group in which the halogen substituent is fluorine or chlorine; q=0; T represents a chlorine atom, a fluoroalkyl or fluoroalkoxy group of 1 to 4 carbon atoms and 1 to 5 fluorine atoms, or a trifluoromethylphenoxy group in which the phenoxy moiety can also bear one or more fluorine, chlorine or bromine atoms; each Y independently represents a fluorine or chlorine atom; and p=0, 1, 2, 3 or 4.

The —COOR substituent in the phenylthio group of the benzoylureas of formula I may be located in any one of the available positions on the phenyl ring but it is preferably located in the 2-position.

The invention also provides a process for preparing the novel benzoylurea compounds, which comprises reacting a benzoylisocyanate of formula:

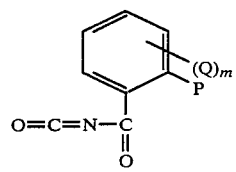

(III)

with a sulphenamide of formula:

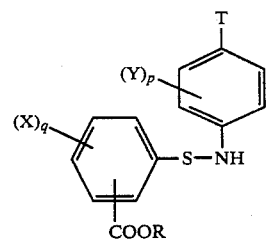

(IV)

in which P, Q, m, R, X, q, T, Y and p have the meanings specified above.

The reaction is suitably carried out in the presence of a solvent. Suitable solvents are aromatic solvents such as benzene, toluene, xylene, or chlorobenzene, hydrocarbons such as petroleum fractions, chlorinated hydrocarbons such as chloroform, methylene chloride or dichloroethane, and ethers such as diethylether, dibutylether, or dioxan. Mixtures of solvents are also suitable.

Preferably the reaction is carried out at a temperature from 0° C. to 100° C., suitably ambient temperature. Preferably the molar ratio of benzoyl-isocyanate to sulphenamide is from 1:1 to 2:1. Preferably the reaction is carried out under anhydrous conditions.

The sulphenamide intermediates IV are themselves novel and constitute a further aspect of the invention; they may be prepared by reacting sulphenyl halide of formula:

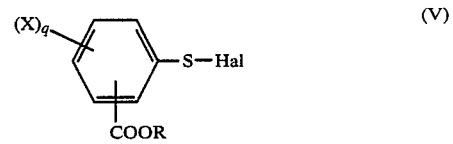

(V)

wherein X, q and R have the meanings specified above in relation to formula I and Hal represents a halogen atom, preferably a chlorine or bromine atom, with an aniline of formula:

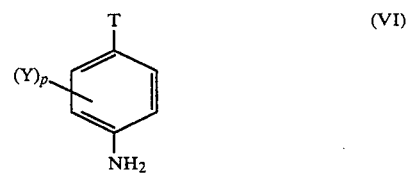

(VI)

wherein T, Y and p have the meanings specified above in relation to formula I in the presence of a dehydrohalogenating agent, such as an organic or inorganic base. Suitable bases include alkali metal hydroxides, amides or alkoxides, for example, sodium ethoxide; alkali metal or alkaline earth metal hydroxides, for example, potassium hydroxide; and primary, secondary or tertiary amines, for example, triethylamine or piperidine.

The reaction is conveniently carried out in the presence of an aprotic solvent; suitable solvents include aromatic solvents such as benzene, toluene, xylene or chlorobenzene, hydrocarbons such as petroleum, chlorinated hydrocarbons, such as methylene chloride, and ethers such as diethylether and dibutylether.

The reaction is suitably carried out at a temperature in the range of −10° to 50° C., preferably −5° to 20° C.

The sulphenyl halide of formula V may be prepared from the corresponding thio or disulphide, e.g. according to the method of L. Katz, L. S. Karger, W. Schroeder and M. S. Cohen, J. Org. Chem., 1953, 18, 1380. In the preparation of the intermediates IV the sulphenyl halide V starting material may be prepared in situ. The disulphide starting material for the sulphenyl halide of formula V may be prepared by the esterification of the corresponding dicarboxylic acid according to the method of J. C. Grivas, J. Org. Chem. 1975, 40, 2029.

The compounds of the present invention have been found to have high insecticidal and acaricidal activity. Accordingly the present invention also provides pesticidal compositions comprising a compound of formula I as defined above together with a carrier. Such a composition may contain a single compound or a mixture of several compounds of the invention. The invention further provides a method of combating pests at a locus, which comprises applying an insecticidally effective amount of a benzoylurea compound or composition according to the present invention to the locus.

Unlike the compounds of the prior art, which are virtually insoluble in organic solvents and therefore extremely difficult to formulate without great expense, the compounds of the general formula I are in general readily soluble in organic solvents making formulation relatively simple, and the resulting compositions easy to handle and economically attractive. The compounds of the general formula I also appear to possess a faster mode of action than the compounds of the prior art.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated from which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The composition of the invention may also contain other ingredients, for example, other compounds possessing pesticidal properties. Further insecticidal compounds may be included, particularly such compounds having a different mode of activity.

The following Examples illustrate the invention. Example A is concerned with the synthesis of a novel sulphenamide starting material, Examples 1-63 are concerned with the synthesis of the novel benzoylureas, and Example 64 with the biological activity of the novel benzoylureas. Examples 65 to 114 give details of novel intermediates of the general formula IV.

EXAMPLE A

Preparation of isopropyl 2-[[[4-(trifluoromethoxy)phenyl]amino]thio]benzoate

A solution of bromine (0.65 ml) in dry methylene chloride (10 ml) was added over thirty minutes to a stirred solution of diisopropyl 2,2'-dithiobisbenzoate (4.9 g) in the same solvent (40 ml) at ambient temperature. The resulting dark red solution was stirred at this temperature for 1.25 hours and was then added over thirty minutes to a stirred solution of 4-(trifluoromethoxy)aniline (4.45 g) in dry methylene chloride (100 ml) containing triethylamine (5.0 ml). The temperature of the reaction mixture was kept at 5°-10° C. throughout the addition by means of an ice bath and when the addition had been completed, the reaction was allowed to warm to ambient temperature over 4.0 hours. The solvent was removed under reduced pressure and the residue was suspended in diethyl ether (250 ml) and washed with water to remove triethylamine hydrobromide. The resulting diethyl ether solution was dried using magnesium sulphate and evaporated to yield the crude product which was purified by crystallisation from diethyl ether/light petroluem.

The crystallisation yielded 7.4 g of the desired product as colourless plates, melting point 120°-121° C.

The following analytical results were obtained:
Calculated: C: 55.0%, H: 4.3%, N: 3.8%. Found: C: 55.0%, H: 4.5%, N: 3.8%.

EXAMPLE 1

Preparation of isopropyl 2-[[[[(2-chlorobenzoyl)amino]carbonyl][4-(trifluoromethoxy)phenyl]amino]thio]benzoate A solution of 2-chlorobenzoyl isocyanate (2.7 g) in dry toluene (5.0 ml) was added to a stirred suspension of isopropyl 2-[[[4-(trifluoromethoxy)phenyl]amino]thio]benzoate (3.7 g) in the same solvent (20.0 ml) at room temperature. After 18 hours, a cake of crystals had formed. The reaction mixture was cooled to −5° C. and filtered, washing the crystals with cold toluene followed by light petroleum. After drying at 40° C. under vacuum, the pure product was obtained as colourless crystals (4.8 g). Melting point 143°-144° C.

The following analytical results were obtained:
Calculated: C: 54.3%, H: 3.7%, N: 5.1%. Found: C: 54.5%, H: 3.5%, N: 5.2%.

EXAMPLE 2

Preparation of butyl 2-[[[[(2,6-difluorobenzoyl)amino]carbonyl][4-(trifluoromethyl)phenyl]amino]thio]benzoate A solution of 2,6-difluorobenzoyl isocyanate (1.1 g) in dry toluene (5.0 ml) was added to a stirred solution of butyl 2-[[[4-(trifluoromethyl)phenyl]amino]thio]benzoate (1.9 g) in the same solvent (7.0 ml) at room temperature. After 18 hours, the reaction mixture was cooled to −5°, and the crystalline precipitate was separated, washing with cold toluene followed by light petroleum. The pure product was obtained as colourless crystals (2.5 g, melting point 79°-81°) after recrystallisation from diethyl ether/light petroleum.

The following analytical results were obtained:
Calculated: C: 56.5%, H: 3.8%, N: 5.1%. Found: C: 56.3%, H: 4.0%, N: 5.1%.

EXAMPLE 3

Preparation of propyl 2-[[[4-[2-chloro-4-(trifluoromethyl)phenoxy-phenyl][[(2,6-difluorobenzoyl)amino]carboxyl]amino-thio]benzoate A solution of 2,6-difluorobenzoyl isocyanate (1.8 g) in dry toluene (5.0 ml) was added to a stirred solution of propyl 2-[[[[2-chloro-4-(trifluoromethyl)phenoxy]-phenyl]amino]thio]benzoate (3.6 g) in the same solvent (7.0 ml) at room temperature. After 4.0 hours, the reaction mixture was evaporated under reduced pressure and the product was isolated from the residue by rapid chromatography on silica gel using methylene chloride as eluent. Crystallisation from diethyl ether/light petroleum afforded the pure product as colourless crystals (4.2 g) melting point 148°-150°.

The following analytical results were obtained:
Calculated: C: 56.0%, H: 3.3%, N: 4.2%. Found: C: 56.3%, H: 3.3%, N: 4.3%.

EXAMPLE 4

Preparation of ethyl 2-[[[[(2-chlorobenzoyl)amino]carbonyl][4-[2-chloro-4-(trifluoromethyl)phenoxy]phenyl]amino]thio]benzoate A solution of 2-chlorobenzoyl isocyanate (1.8 g) in dry toluene (5.0 ml) was added to a stirred solution of ethyl 2-[[[[(2-chloro-4-(trifluoromethyl)phenoxy]-phenyl]amino]thio]benzoate (3.5 g) in the same solvent (7.0 ml) at room temperature. After 18.0 hours, the reaction mixture was diluted with dry light petroleum (30 ml) and the resulting precipitate of crude product was separated, washing with light petroleum. This material was purified by rapid chromatography on silica gel followed by crystallisation from diethyl ether/light petroleum.

The crystallisation yielded 3.1 g of the desired product as colourless crystals, melting point 98°-100° C.

The following analytical results were obtained:
Calculated: C: 55.5%, H: 3.2%, N: 4.3%. Found: C: 55.6%, H: 3.2%, N: 4.3%.

EXAMPLES 5 TO 63

In Examples 5 to 63 compounds were prepared by one of the methods described in Examples 1 to 4.

The compounds, their melting points and chemical analyses are shown in Table 1 below.

TABLE 1

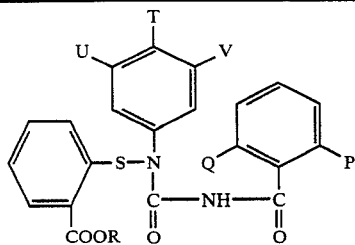

| Example No. | T | R | P | Q | U | V | m.p. (°C.) | | Analysis % C | H | N |
|---|---|---|---|---|---|---|---|---|---|---|---|
| 5 | 2-Cl—4-CF₃—C₆H₃—O— | Sec-C₄H₉— | F | F | H | H | 77–79 | Calc. | 56.6 | 3.5 | 4.1 |
| | | | | | | | | Found. | 56.8 | 3.9 | 4.0 |
| 6 | —OCF₃ | CH₃ | Cl | H | H | H | 144–145 | Calc. | 52.6 | 3.1 | 5.3 |
| | | | | | | | | Found. | 52.7 | 2.9 | 4.8 |
| 7 | —OCF₃ | C₂H₅ | Cl | H | H | H | 150–152 | Calc. | 53.5 | 3.4 | 5.2 |
| | | | | | | | | Found. | 53.6 | 3.2 | 5.3 |
| 8 | —OCF₃ | n-C₃H₇ | Cl | H | H | H | 122–123 | Calc. | 54.3 | 3.7 | 5.1 |
| | | | | | | | | Found. | 54.5 | 3.6 | 5.2 |
| 9 | —OCF₃ | n-C₄H₉ | Cl | H | H | H | 111–113 | Calc. | 55.1 | 3.9 | 4.9 |
| | | | | | | | | Found. | 55.1 | 3.7 | 5.0 |
| 10 | —OCF₃ | —CH(CH₃)CH₂CH₃ | Cl | H | H | H | 118–119 | Calc. | 55.1 | 3.9 | 4.9 |
| | | | | | | | | Found. | 54.8 | 3.7 | 5.0 |
| 11 | —OCF₃ | n-C₅H₁₁ | Cl | H | H | H | 88–89 | Calc. | 55.8 | 4.2 | 4.8 |
| | | | | | | | | Found. | 55.9 | 3.7 | 5.2 |
| 12 | —OCF₃ | —CH(CH₃)CH₂CH₂CH₃ | Cl | H | H | H | 119–120 | Calc. | 55.8 | 4.2 | 4.8 |
| | | | | | | | | Found. | 55.8 | 3.8 | 5.0 |
| 13 | —CF₃ | CH₃ | F | F | H | H | 161–163 | Calc. | 54.1 | 2.9 | 5.5 |
| | | | | | | | | Found. | 54.8 | 3.5 | 5.4 |
| 14 | —CF₃ | C₂H₅ | F | F | H | H | 137–140 | Calc. | 55.0 | 3.2 | 5.3 |
| | | | | | | | | Found. | 55.4 | 3.1 | 5.5 |
| 15 | —CF₃ | n-C₃H₇ | F | F | H | H | 140–143 | Calc. | 55.8 | 3.5 | 5.2 |
| | | | | | | | | Found. | 55.5 | 3.4 | 5.3 |
| 16 | —CF₃ | i-C₃H₇ | F | F | H | H | 155–157 | Calc. | 55.8 | 3.5 | 5.2 |
| | | | | | | | | Found. | 55.7 | 3.4 | 5.4 |
| 17 | —CF₃ | (CH₂)₂CH(CH₃)₂ | F | F | H | H | 139–141 | Calc. | 57.2 | 4.1 | 5.0 |
| | | | | | | | | Found. | 58.1 | 4.0 | 4.9 |
| 18 | —CF₃ | CH₂CF₃ | F | F | H | H | 80–82 | Calc. | 49.8 | 2.4 | 4.8 |
| | | | | | | | | Found. | 50.4 | 2.4 | 4.8 |
| 19 | 2-Cl—4-CF₃—C₆H₃—O— | CH₃ | F | F | H | H | 135–137 | Calc. | 54.7 | 2.8 | 4.4 |
| | | | | | | | | Found. | 54.9 | 2.8 | 4.5 |
| 20 | 2-Cl—4-CF₃—C₆H₃—O— | C₂H₅ | F | F | H | H | 126–128 | Calc. | 55.3 | 3.1 | 4.3 |
| | | | | | | | | Found. | 55.5 | 3.0 | 4.3 |
| 21 | 2-Cl—4-CF₃—C₆H₃—O— | n-C₄H₉ | F | F | H | H | 124–126 | Calc. | 56.6 | 3.5 | 4.1 |
| | | | | | | | | Found. | 56.7 | 3.4 | 4.2 |
| 22 | 2-Cl—4-CF₃—C₆H₃—O— | —CH(CH₃)CH₂CH₃ | F | F | H | H | 77–79 | Calc. | 56.6 | 3.5 | 4.1 |
| | | | | | | | | Found. | 56.8 | 3.9 | 4.0 |
| 23 | 2-Cl—4-CF₃—C₆H₃—O— | n-C₅H₁₁ | F | F | H | H | 63–65 | Calc. | 57.2 | 3.8 | 4.0 |
| | | | | | | | | Found. | 56.7 | 3.5 | 4.1 |
| 24 | 2-Cl—4-CF₃—C₆H₃—O— | —CH(CH₃)CH₂CH₂CH₃ | F | F | H | H | 70–72 | Calc. | 57.2 | 3.8 | 4.0 |
| | | | | | | | | Found. | 57.2 | 3.9 | 4.3 |
| 25 | 2-Cl—4-CF₃—C₆H₃—O— | CH₃ | Cl | H | H | H | 139–141 | Calc. | 54.8 | 3.0 | 4.4 |
| | | | | | | | | Found. | 54.3 | 3.1 | 4.6 |
| 26 | 2-Cl—4-CF₃—C₆H₃—O— | n-C₃H₇ | Cl | H | H | H | 135–137 | Calc. | 56.1 | 3.5 | 4.2 |
| | | | | | | | | Found. | 56.1 | 3.6 | 4.2 |
| 27 | 2-Cl—4-CF₃—C₆H₃—O— | n-C₄H₉ | Cl | H | H | H | 119–121 | Calc. | 56.7 | 3.7 | 4.1 |
| | | | | | | | | Found. | 56.7 | 3.4 | 4.1 |
| 28 | 2-Cl—4-CF₃—C₆H₃—O— | —(CH₂)₂CH(CH₃)₂ | F | F | H | H | Gum | Calc. | 57.2 | 3.8 | 4.0 |
| | | | | | | | | Found. | 56.7 | 4.1 | 3.8 |
| 29 | 2-Cl—4-CF₃—C₆H₃—O— | —(CH₂)₉CH₃ | F | F | H | H | 48–52 | Calc. | 59.8 | 4.7 | 3.7 |
| | | | | | | | | Found. | 59.5 | 5.0 | 3.6 |
| 30 | 2-Cl—4-CF₃—C₆H₃—O— | —(CH₂)₁₃CH₃ | F | F | H | H | Gum | Calc. | 61.6 | 5.4 | 3.4 |
| | | | | | | | | Found. | 61.6 | 5.7 | 3.4 |
| 31 | 2-Cl—4-CF₃—C₆H₃—O— | —(CH₂)₁₅CH₃ | F | F | H | H | Gum | Calc. | 62.4 | 5.7 | 3.3 |
| | | | | | | | | Found. | 62.0 | 5.8 | 3.4 |
| 32 | 2-Cl—4-CF₃—C₆H₃—O— | cyclohexyl | F | F | H | H | 98–100 | Calc. | 57.4 | 3.7 | 4.0 |
| | | | | | | | | Found. | 58.3 | 4.1 | 3.9 |
| 33 | 2-Cl—4-CF₃—C₆H₃—O— | benzyl | F | F | H | H | 88–91 | Calc. | 59.0 | 3.1 | 3.9 |
| | | | | | | | | Found. | 58.8 | 3.0 | 3.8 |
| 34 | 2-Cl—4-CF₃—C₆H₂—O— | phenyl | F | F | H | H | 96–99 | Calc. | 58.4 | 2.9 | 4.0 |
| | | | | | | | | Found. | 58.6 | 3.0 | 4.0 |
| 35 | 2-Cl—4-CF₃—C₆H₃—O— | —CH(CH₃)CO₂C₂H₅ | F | F | H | H | 81–84 | Calc. | 54.8 | 3.3 | 3.9 |
| | | | | | | | | Found. | 55.0 | 3.3 | 3.8 |
| 36 | 2-Cl—4-CF₃—C₆H₃—O— | —CH₂CO₂C₂H₅ | F | F | H | H | 78–80 | Calc. | 54.2 | 3.1 | 4.0 |
| | | | | | | | | Found. | 54.4 | 3.0 | 3.9 |
| 37 | 2-Cl—4-CF₃—C₆H₃—O— | 2-tetrahydrofuryl-methyl | F | F | H | H | 83–86 | Calc. | 56.1 | 3.4 | 4.0 |
| | | | | | | | | Found. | 55.8 | 3.4 | 4.2 |
| 38 | Cl | n-C₃H₇ | F | F | H | H | 105–108 | Calc. | 57.1 | 3.8 | 5.6 |

TABLE 1-continued

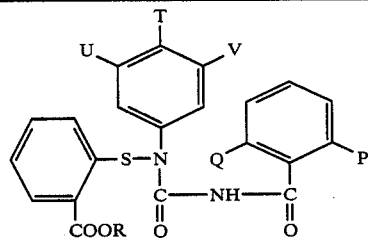

| Example No. | T | R | P | Q | U | V | m.p. (°C.) | | Analysis % C | H | N |
|---|---|---|---|---|---|---|---|---|---|---|---|
| 39 | Cl | Sec-C$_4$H$_9$ | F | F | H | H | 75–78 | Found. | 56.6 | 3.6 | 5.6 |
| | | | | | | | | Calc. | 57.9 | 4.1 | 5.4 |
| | | | | | | | | Found. | 57.7 | 4.1 | 5.4 |
| 40 | OCF$_3$ | n-C$_3$H$_7$ | F | Cl | H | H | 124–125 | Calc. | 52.6 | 3.3 | 4.9 |
| | | | | | | | | Found. | 52.7 | 3.2 | 4.0 |
| 41 | OCF$_3$ | Sec-C$_4$H$_9$ | F | Cl | H | H | 99–100 | Calc. | 53.4 | 3.6 | 4.8 |
| | | | | | | | | Found. | 53.7 | 3.9 | 4.7 |
| 42 | OCF$_3$ | n-C$_3$H$_7$ | F | F | H | H | 98–100 | Calc. | 54.1 | 3.4 | 5.0 |
| | | | | | | | | Found. | 53.7 | 3.5 | 5.3 |
| 43 | OCF$_3$ | Sec-C$_4$H$_9$ | F | F | H | H | 109–110 | Calc. | 54.9 | 3.7 | 4.9 |
| | | | | | | | | Found. | 55.1 | 4.0 | 4.9 |
| 44 | CF$_3$ | C$_2$H$_5$ | F | Cl | H | H | 145–147 | Calc. | 53.3 | 3.2 | 5.2 |
| | | | | | | | | Found. | 53.4 | 3.3 | 5.2 |
| 45 | 2-Cl—4-CF$_3$—C$_6$H$_3$—O— | —CH$_2$CH$_2$OCH$_3$ | F | F | H | H | 85–86 | Calc. | 54.7 | 3.2 | 4.1 |
| | | | | | | | | Found. | 54.9 | 3.1 | 4.2 |
| 46 | 2-Cl—4-CF$_3$—C$_6$H$_3$—O— | —CH$_2$CH$_2$OC$_2$H$_5$ | F | F | H | H | 64–66 | Calc. | 55.3 | 3.5 | 4.0 |
| | | | | | | | | Found. | 55.2 | 3.2 | 4.3 |
| 47 | 2-Cl—4-CF$_3$—C$_6$H$_3$—O— | —(CH$_2$CH$_2$O)$_2$CH$_3$ | F | F | H | H | 86–87 | Calc. | 54.7 | 3.6 | 3.9 |
| | | | | | | | | Found. | 54.7 | 3.5 | 3.9 |
| 48 | 2-Cl—4-CF$_3$—C$_6$H$_3$—O— | —(CH$_2$CH$_2$O)$_2$C$_2$H$_5$ | F | F | H | H | 52–56 | Calc. | 55.2 | 3.8 | 3.8 |
| | | | | | | | | Found. | 54.9 | 3.9 | 3.9 |
| 49 | 3-Cl—4-CN—C$_6$H$_3$—O— | n-C$_3$H$_7$ | Cl | H | Cl | Cl | 111–114 | Calc. | 54.0 | 3.1 | 6.1 |
| | | | | | | | | Found. | 53.3 | 3.1 | 5.8 |
| 50 | 3-Cl—4-CN—C$_6$H$_3$—O— | Sec-C$_4$H$_9$ | Cl | H | Cl | Cl | 99–101 | Calc. | 54.6 | 3.3 | 6.0 |
| | | | | | | | | Found. | 53.9 | 3.3 | 5.7 |
| 51 | 4-CN—C$_6$H$_4$—O— | n-C$_3$H$_7$ | Cl | H | Cl | H | 98–99 | Calc. | 60.0 | 3.7 | 6.8 |
| | | | | | | | | Found. | 59.6 | 3.6 | 6.6 |
| 52 | 4-CN—C$_6$H$_4$—O— | Sec-C$_4$H$_7$ | Cl | H | Cl | H | 114–116 | Calc. | 60.6 | 3.4 | 6.6 |
| | | | | | | | | Found. | 60.3 | 3.8 | 6.4 |
| 53 | 4-NO$_2$—C$_6$H$_4$—O— | n-C$_3$H$_7$ | Cl | H | Cl | Cl | 122–124 | Calc. | 53.4 | 3.3 | 6.2 |
| | | | | | | | | Found. | 53.4 | 3.2 | 6.1 |
| 54 | 3,5-dichloro-2-pyridyloxy | Sec-C$_4$H$_9$ | F | F | Cl | H | 112–115 | Calc. | 52.9 | 3.2 | 6.2 |
| | | | | | | | | Found. | 52.8 | 3.3 | 5.9 |
| 55 | 3,5-dichloro-2-pyridyloxy | n-C$_3$H$_7$ | F | F | Cl | H | 110–112 | Calc. | 52.2 | 3.0 | 6.3 |
| | | | | | | | | Found. | 52.5 | 3.1 | 5.9 |
| 56 | 3,5-dichloro-2-pyridyloxy | Sec-C$_4$H$_9$ | F | F | Cl | Cl | 140–142 | Calc. | 50.3 | 2.9 | 5.9 |
| | | | | | | | | Found. | 49.9 | 3.0 | 6.0 |
| 57 | 3,5-dichloro-2-pyridyloxy | n-C$_3$H$_7$ | F | F | Cl | Cl | 158–160 | Calc. | 49.6 | 2.7 | 6.0 |
| | | | | | | | | Found. | 49.8 | 2.6 | 6.0 |
| 58 | 4-NO$_2$—C$_6$H$_4$—O— | n-C$_3$H$_7$ | F | F | Cl | Cl | 115–118 | Calc. | 53.3 | 3.1 | 6.2 |
| | | | | | | | | Found. | 52.8 | 2.9 | 6.2 |
| 59 | 4-NO$_2$—C$_6$H$_4$—O— | Sec-C$_4$H$_9$ | F | F | Cl | Cl | 113–116 | Calc. | 53.9 | 3.3 | 6.1 |
| | | | | | | | | Found. | 53.8 | 3.3 | 5.9 |
| 60 | 4-NO$_2$—C$_6$H$_4$—O— | n-C$_5$H$_{11}$ | F | F | Cl | Cl | 105–108 | Calc. | 54.5 | 3.6 | 6.0 |
| | | | | | | | | Found. | 54.5 | 3.6 | 5.9 |
| 61 | 4-NO$_2$—C$_6$H$_4$—O— | n-C$_4$H$_9$ | F | F | Cl | Cl | 100–103 | Calc. | 53.9 | 3.3 | 6.1 |
| | | | | | | | | Found. | 54.2 | 3.4 | 5.9 |
| 62 | 4-NO$_2$—C$_6$H$_4$—O— | n-C$_4$H$_9$ | F | Cl | Cl | Cl | 147–149 | Calc. | 52.7 | 3.3 | 5.9 |
| | | | | | | | | Found. | 52.5 | 2.9 | 5.9 |
| 63 | 4-NO$_2$—C$_6$H$_4$—O— | n-C$_5$H$_{11}$ | F | Cl | Cl | Cl | 165 | Calc. | 53.3 | 3.5 | 5.8 |
| | | | | | | | | Found. | 53.6 | 3.4 | 5.8 |

EXAMPLE 64

The insecticidal activity of the benzoylurea compounds of the invention was determined in the following tests.

Test 1

The insecticidal and ovicidal activities of the compounds of the invention were assessed employing the pests Spodoptera littoralis (S.l.), Aedes aegypti (A.a) and eggs of Spodoptera littoralis (S.l.ov).

The test methods used for each species appear below. In each case the tests were conducted under normal conditions (23° C.±2° C.; fluctuating light and humidity).

In each test an LC$_{50}$ for the compound was calculated from the mortality figures and compared with the corresponding LC$_{50}$ for ethyl parathion in the same tests. The results are expressed as toxicity indices thus:

$$\text{toxicity indices} = \frac{LC_{50} \text{ (parathion)}}{LC_{50} \text{ (test compound)}} \times 100$$

and are set out in Table 2 below.

(i) *Spodoptera Littoralis*

Solutions or suspensions of the compound were made up over a range of concentrations in 10% acetone/water containing 0.025% Triton X100 ("Triton" is a registered trade mark). These solutions were sprayed using a logarithmic spraying machine onto petri dishes containing a nutritious diet on which the *Spodoptera littoralis* larvae had been reared. When the spray deposit had dried each dish was infested with 10 2nd instar larvae. Mortality assessments were made 7 days after spraying.

(ii) *Aedes aegypti*

Several solutions of the test compound of varying concentration were prepared in acetone. 100 microliter quantities were added to 100 ml of tap water, the acetone being allowed to evaporate off. 10 early 4th instar larvae were placed in the test solution; after 48 hours the (surviving) larvae were fed with animal feed pellets, and the final percentage mortality assessed when all the larvae had either pupated and emerged as adults or died.

(iii) *Spodoptera littoralis* (ovicide)

Solutions as described in (i) above were prepared. Eggs less than 24 hours old were obtained as follows. Adult *Spodoptera littoralis* were held in large plastic cylinders containing blotting paper on which the moths laid their batches of eggs. Egg batches containing approximately 60-70 eggs were cut from the blotting paper with a 1 cm surround. These were placed eggs uppermost on filter paper in the deeper half of 5 cm disposable petri dishes and each batch of eggs was then sprayed with a different test solution or the control solution. The dishes were covered until the control eggs had hatched, approximately 5 days. The percentage ovicidal mortality was then calculated. In Table 2, a dash indicates no results available.

TABLE 2

| Compound of Example | S.l. | Test Code A.a. | S.l.ov. |
|---|---|---|---|
| 1 | 490 | 160 | 830 |
| 2 | 160 | 72 | 3,100 |
| 3 | 2,400 | 160 | — |
| 4 | 2,450 | 130 | — |
| 5 | 2,400 | 250 | — |
| 6 | 190 | 210 | 670 |
| 7 | 74 | 130 | 390 |
| 8 | 150 | 72 | 970 |
| 9 | 400 | 150 | 840 |
| 10 | 88 | 72 | 400 |
| 11 | 106 | 76 | 900 |

TABLE 2-continued

| Compound of Example | S.l. | Test Code A.a. | S.l.ov. |
|---|---|---|---|
| 12 | 131 | 64 | 630 |
| 13 | 120 | 100 | 625 |
| 14 | 150 | 220 | 1,200 |
| 15 | 180 | 140 | 1,100 |
| 16 | 75 | 150 | 2,700 |
| 17 | 188 | 140 | 620 |
| 18 | 81 | 62 | 100 |
| 19 | 1,900 | 400 | — |
| 20 | 2,200 | 240 | — |
| 21 | 1,800 | 300 | — |
| 22 | 2,400 | 250 | — |
| 23 | 2,320 | 160 | — |
| 24 | 1,690 | 4 | — |
| 25 | 1,500 | 170 | — |
| 26 | 1,400 | 95 | — |
| 27 | 1,900 | 71 | — |
| 28 | 2,300 | 650 | — |
| 29 | 3,700 | 230 | — |
| 30 | 940 | 110 | — |
| 31 | 1,700 | 12 | — |
| 32 | 1,500 | 1,500 | — |
| 33 | 1,700 | 16 | — |
| 34 | 2,200 | 1,000 | — |
| 35 | 1,900 | 460 | — |
| 36 | 2,300 | 300 | — |
| 37 | 1,100 | — | — |
| 38 | 49 | 110 | 2,400 |
| 39 | 49 | 130 | 500 |
| 40 | 270 | 76 | 39 |
| 41 | 210 | 79 | — |
| 42 | 160 | 130 | 2,500 |
| 43 | 150 | 250 | 860 |
| 44 | 94 | 82 | — |
| 45 | 2,500 | 780 | — |
| 46 | 1,4750 | 850 | — |
| 47 | 1,860 | 860 | — |
| 48 | 1,180 | 670 | — |
| 49 | 430 | 110 | — |
| 50 | 120 | 110 | — |
| 51 | 170 | 85 | — |
| 52 | 75 | 88 | — |
| 53 | 1,200 | 150 | — |
| 54 | 960 | 1,500 | — |
| 55 | 1,000 | 240 | — |
| 56 | 2,100 | 1,400 | — |
| 57 | 1,100 | 350 | — |
| 58 | 2,000 | 580 | — |
| 59 | 1,200 | 530 | — |
| 60 | 1,800 | 500 | — |
| 61 | 2,100 | 210 | — |
| 62 | | | |
| 63 | | | |

EXAMPLES 65 TO 114

Novel sulphenamide starting materials of the general formula IV were used in the synthesis of the compounds of Examples 1 to 63. Table 3 gives the physical data for each of these novel sulphenamides, which were prepared by the general method illustrated by Example A above.

TABLE 3

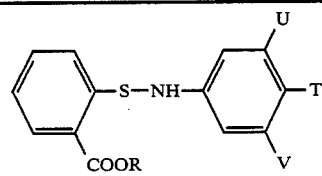

| Example No. | T | R | U | V | m.p. (°C.) | Analysis % C | H | N |
|---|---|---|---|---|---|---|---|---|
| 65 | OCF$_3$ | i-C$_3$H$_7$ | H | H | 120-121 | Calc. 55.0 | 4.3 | 3.8 |
| | | | | | | Found. 55.0 | 4.5 | 3.8 |

TABLE 3-continued

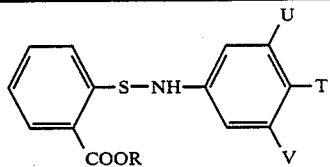

| Example No. | T | R | U | V | m.p. (°C.) | | Analysis % C | H | N |
|---|---|---|---|---|---|---|---|---|---|
| 66 | CF$_3$ | n-C$_4$H$_9$ | H | H | 115–117 | Calc. | 58.5 | 4.9 | 3.8 |
|  |  |  |  |  |  | Found. | 58.4 | 4.9 | 3.8 |
| 67 | 2-Cl—4-CF$_3$—phenoxy | n-C$_3$H$_7$ | H | H | 117–119 | Calc. | 57.3 | 4.0 | 2.9 |
|  |  |  |  |  |  | Found. | 57.4 | 3.9 | 2.9 |
| 68 | 2-Cl—4-CF$_3$—phenoxy | C$_2$H$_5$ | H | H | 120–122 | Calc. | 56.5 | 3.6 | 3.0 |
|  |  |  |  |  |  | Found. | 56.3 | 3.7 | 3.0 |
| 69 | 2-Cl—4-CF$_3$—phenoxy | Sec-C$_4$H$_9$ | H | H | 112–115 | Calc. | 58.1 | 4.2 | 2.8 |
|  |  |  |  |  |  | Found. | 58.0 | 4.3 | 2.8 |
| 70 | OCF$_3$ | CH$_3$ | H | H | 100–101 | Calc. | 52.5 | 3.5 | 4.1 |
|  |  |  |  |  |  | Found. | 52.6 | 3.5 | 4.1 |
| 71 | OCF$_3$ | C$_2$H$_5$ | H | H | 123–125 | Calc. | 53.8 | 4.0 | 3.9 |
|  |  |  |  |  |  | Found. | 54.0 | 4.1 | 4.0 |
| 72 | OCF$_3$ | n-C$_3$H$_7$ | H | H | 132–134 | Calc. | 55.0 | 4.3 | 3.8 |
|  |  |  |  |  |  | Found. | 55.2 | 4.3 | 3.9 |
| 73 | OCF$_3$ | n-C$_4$H$_7$ | H | H | 123–124 | Calc. | 56.1 | 4.7 | 3.6 |
|  |  |  |  |  |  | Found. | 56.0 | 4.9 | 3.7 |
| 74 | OCF$_3$ | Sec-C$_4$H$_9$ | H | H | 98–99 | Calc. | 56.1 | 4.7 | 3.6 |
|  |  |  |  |  |  | Found. | 56.3 | 4.6 | 3.9 |
| 75 | OCF$_3$ | n-C$_5$H$_{11}$ | H | H | 114–116 | Calc. | 57.1 | 5.1 | 3.5 |
|  |  |  |  |  |  | Found. | 57.1 | 4.7 | 3.7 |
| 76 | OCF$_3$ | —CH(CH$_3$)CH$_2$CH$_2$CH$_3$ | H | H | 85–86 | Calc. | 57.1 | 5.1 | 3.5 |
|  |  |  |  |  |  | Found. | 57.2 | 5.1 | 3.7 |
| 77 | CF$_3$ | CH$_3$ | H | H | 164–166 | Calc. | 55.0 | 3.7 | 4.3 |
|  |  |  |  |  |  | Found. | 54.7 | 3.7 | 4.4 |
| 78 | CF$_3$ | C$_2$H$_5$ | H | H | 123–125 | Calc. | 56.3 | 4.1 | 4.1 |
|  |  |  |  |  |  | Found. | 56.2 | 4.1 | 4.2 |
| 79 | CF$_3$ | n-C$_3$H$_7$ | H | H | 129–132 | Calc. | 57.5 | 4.5 | 3.9 |
|  |  |  |  |  |  | Found. | 57.7 | 4.6 | 4.0 |
| 80 | CF$_3$ | i-C$_3$H$_7$ | H | H | 133–135 | Calc. | 57.5 | 4.5 | 3.9 |
|  |  |  |  |  |  | Found. | 57.3 | 4.6 | 4.0 |
| 81 | CF$_3$ | —(CH$_2$)$_2$CH(CH$_3$)$_2$ | H | H | 142–144 | Calc. | 59.5 | 5.2 | 3.7 |
|  |  |  |  |  |  | Found. | 59.4 | 5.3 | 3.8 |
| 82 | CF$_3$ | —CH$_2$CF$_3$ | H | H | 104–107 | Calc. | 48.6 | 2.8 | 3.5 |
|  |  |  |  |  |  | Found. | 48.5 | 2.8 | 3.4 |
| 83 | 2-Cl—4-CF$_3$—phenoxy | CH$_3$ | H | H | 132–134 | Calc. | 55.6 | 3.3 | 3.1 |
|  |  |  |  |  |  | Found. | 55.6 | 3.3 | 3.1 |
| 84 | 2-Cl—4-CF$_3$—phenoxy | n-C$_4$H$_9$ | H | H | 103–104 | Calc. | 58.1 | 4.2 | 2.8 |
|  |  |  |  |  |  | Found. | 58.3 | 4.4 | 2.9 |
| 85 | 2-Cl—4-CF$_3$—phenoxy | n-C$_5$H$_{11}$ | H | H | 98–100 | Calc. | 58.9 | 4.5 | 2.7 |
|  |  |  |  |  |  | Found. | 58.7 | 4.5 | 2.7 |
| 86 | 2-Cl—4-CF$_3$—phenoxy | —CH(CH$_3$)CH$_2$CH$_2$CH$_3$ | H | H | 89–91 | Calc. | 58.9 | 4.5 | 2.7 |
|  |  |  |  |  |  | Found. | 58.6 | 4.6 | 2.7 |
| 87 | 2-Cl—4-CF$_3$—phenoxy | —CH$_2$CH$_2$CH(CH$_3$)$_2$ | H | H | not isolated | Calc. | 58.9 | 4.5 | 2.7 |
|  |  |  |  |  |  | Found. |  |  |  |
| 88 | 2-Cl—4-CF$_3$—phenoxy | —(CH$_2$)$_9$CH$_3$ | H | H | 92–95 | Calc. | 62.1 | 5.7 | 2.4 |
|  |  |  |  |  |  | Found. | 62.2 | 5.9 | 2.3 |
| 89 | 2-Cl—4-CF$_3$—phenoxy | —(CH$_2$)$_{13}$CH$_3$ | H | H | 101–103 | Calc. | 64.2 | 6.5 | 2.2 |
|  |  |  |  |  |  | Found. | 64.6 | 6.3 | 2.1 |
| 90 | 2-Cl—4-CF$_3$—phenoxy | —(CH$_2$)$_{15}$CH$_3$ | H | H | 98–100 | Calc. | 65.1 | 6.8 | 2.1 |
|  |  |  |  |  |  | Found. | 65.0 | 7.1 | 2.0 |
| 91 | 2-Cl—4-CF$_3$—phenoxy | cyclohexyl | H | H | 138–140 | Calc. | 59.8 | 4.4 | 2.7 |
|  |  |  |  |  |  | Found. | 59.9 | 4.5 | 2.6 |
| 92 | 2-Cl—4-CF$_3$—phenoxy | benzyl | H | H | 114–116 | Calc. | 61.2 | 3.6 | 2.6 |
|  |  |  |  |  |  | Found. | 61.7 | 3.7 | 2.6 |
| 93 | 2-Cl—4-CF$_3$—phenoxy | phenyl | H | H | 128–130 | Calc. | 60.5 | 3.3 | 2.7 |
|  |  |  |  |  |  | Found. | 60.4 | 3.3 | 2.7 |
| 94 | 2-Cl—4-CF$_3$—phenoxy | —CH(CH$_3$)CO$_2$C$_2$H$_5$ | H | H | 109–111 | Calc. | 55.6 | 3.9 | 2.6 |
|  |  |  |  |  |  | Found. | 55.6 | 4.0 | 2.6 |
| 95 | 2-Cl—4-CF$_3$—phenoxy | —CH$_2$CO$_2$C$_2$H$_5$ | H | H | 119–121 | Calc. | 54.8 | 3.6 | 2.7 |
|  |  |  |  |  |  | Found. | 55.0 | 3.7 | 2.7 |
| 96 | 2-Cl—4-CF$_3$—phenoxy | 2-tetrahydrofurylmethyl | H | H | 124–126 | Calc. | 57.3 | 4.0 | 2.7 |
|  |  |  |  |  |  | Found. | 57.3 | 4.1 | 2.7 |
| 97 | Cl | n-C$_3$H$_7$ | H | H | 102–104 | Calc. | 59.7 | 5.0 | 4.4 |
|  |  |  |  |  |  | Found. | 59.8 | 4.9 | 4.4 |
| 98 | Cl | Sec-C$_4$H$_9$ | H | H | 90–93 | Calc. | 60.8 | 5.4 | 4.2 |
|  |  |  |  |  |  | Found. | 60.6 | 5.5 | 4.2 |
| 99 | 2-Cl—4-CF$_3$—phenoxy | —CH$_2$CH$_2$OCH$_3$ | H | H | 107–108 | Calc. | 55.5 | 3.8 | 2.8 |
|  |  |  |  |  |  | Found. | 55.6 | 3.9 | 2.9 |
| 100 | 2-Cl—4-CF$_3$—phenoxy | —CH$_2$CH$_2$OC$_2$H$_5$ | H | H | 103–104 | Calc. | 56.3 | 4.1 | 2.7 |
|  |  |  |  |  |  | Found. | 55.6 | 3.9 | 2.9 |
| 101 | 2-Cl—4-CF$_3$—phenoxy | —(CH$_2$CH$_2$O)$_2$CH$_3$ | H | H | 106–108 | Calc. | 55.4 | 4.2 | 2.6 |

TABLE 3-continued

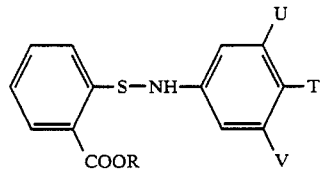

| Example No. | T | R | U | V | m.p. (°C.) | | C | H | N |
|---|---|---|---|---|---|---|---|---|---|
| 102 | 2-Cl—4-CF$_3$—phenoxy | —(CH$_2$CH$_2$O)$_2$C$_2$H$_5$ | H | H | 86–88 | Found. | 55.5 | 4.3 | 2.6 |
| | | | | | | Calc. | 56.2 | 4.5 | 2.5 |
| 103 | 3-Cl—4-CN—phenoxy | n-C$_3$H$_7$ | Cl | Cl | 97–100 | Found. | 55.9 | 4.5 | 2.6 |
| | | | | | | Calc. | 54.4 | 3.3 | 5.5 |
| 104 | 3-Cl—4-CN—phenoxy | Sec-C$_4$H$_9$ | Cl | Cl | 103–105 | Found. | 54.4 | 3.3 | 5.1 |
| | | | | | | Calc. | 55.2 | 3.6 | 5.4 |
| 105 | 4-CN—phenoxy | n-C$_3$H$_7$ | Cl | H | 68–70 | Found. | 55.6 | 3.8 | 5.0 |
| | | | | | | Calc. | 62.9 | 4.3 | 6.4 |
| 106 | 4-CN—phenoxy | Sec-C$_4$H$_9$ | Cl | H | 77–79 | Found. | 62.1 | 4.4 | 6.1 |
| | | | | | | Calc. | 63.7 | 4.6 | 6.2 |
| 107 | 4-NO$_2$—phenoxy | n-C$_3$H$_7$ | Cl | Cl | 85–87 | Found. | 62.9 | 4.8 | 6.0 |
| | | | | | | Calc. | 53.5 | 3.7 | 5.7 |
| 108 | 3,5-dichloro-2-pyridyloxy | Sec-C$_4$H$_7$ | C | H | 116–118 | Found. | 53.6 | 3.7 | 5.8 |
| | | | | | | Calc. | 53.1 | 3.8 | 5.6 |
| 109 | 3,5-dichloro-2-pyridyloxy | n-C$_3$H$_7$ | Cl | H | 141–143 | Found. | 53.0 | 3.56 | 5.6 |
| | | | | | | Calc. | 52.1 | 3.5 | 5.8 |
| 110 | 3,5-dichloro-2-pyridyloxy | Sec-C$_4$H$_9$ | Cl | Cl | 78–80 | Found. | 52.0 | 3.4 | 5.7 |
| | | | | | | Calc. | 49.6 | 3.4 | 5.3 |
| 111 | 3,5-dichloro-2-pyridyloxy | n-C$_3$H$_7$ | Cl | Cl | 153–155 | Found. | 50.5 | 3.3 | 5.0 |
| | | | | | | Calc. | 48.6 | 3.1 | 5.4 |
| 112 | 4-NO$_2$—phenoxy | Sec-C$_4$H$_9$ | Cl | Cl | 131–133 | Found. | 47.8 | 3.0 | 5.3 |
| | | | | | | Calc. | 54.4 | 3.9 | 5.5 |
| 113 | 4-NO$_2$—phenoxy | n-C$_5$H$_{11}$ | Cl | Cl | 132–134 | Found. | 54.4 | 3.9 | 5.5 |
| | | | | | | Calc. | 55.3 | 4.2 | 5.4 |
| 114 | 4-NO$_2$—phenoxy | n-C$_4$H$_9$ | Cl | Cl | 129–130 | Found. | 55.3 | 4.1 | 5.4 |
| | | | | | | Calc. | 54.4 | 3.9 | 5.5 |
| | | | | | | Found. | 54.9 | 4.0 | 5.5 |

I claim:

1. A benzoylurea compound of formula:

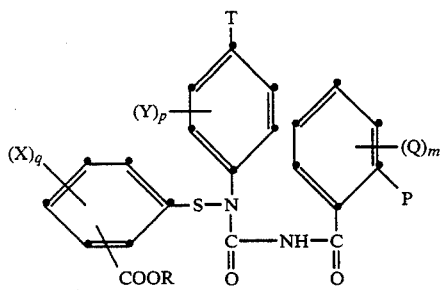

in which each of P and Q independently represents a halogen atom or an alkyl group; m represents 0, 1 or 2; R represents an alkyl, alkenyl or alkynyl group which may be substituted by one or more halogen atoms or one of alkoxy, haloalkoxy, hydroxy, carboxy, alkoxycarbonyl, cycloalkyl, tetrahydrofuryl, a group —O—CH$_2$CH$_2$O)$_n$ alkyl wherein n=1, 2, 3 or 4, or phenyl which may be substituted by halogen, alkyl, haloalkyl, alkoxy, haloalkoxy, alkenyl, haloalkenyl, nitro or cyano; a cycloalkyl group which may be substituted as indicated above, or by alkyl or haloalkyl; or a phenyl group which may be substituted as indicated above; a hydrogen atom; one equivalent of an alkali metal or alkaline earth metal; or an ammonium or $C_1$-$C_6$ alkyl-substituted ammonium group; each X independently represents a halogen atom, a cyano, nitro or carboxy group, or an alkyl, alkoxy, alkylthio, cycloalkyl, cycloalkyloxy, cycloalkylthio, alkenyl, alkenylthio, alkylcarbonyl, alkoxycarbonyl, alkylsulphonyl, alkynyl, phenyl, phenoxy, phenylthio or amino group which groups may be substituted as described for the moiety R, above; q=0, 1, 2, 3 or 4; T represents a halogen atom, an alkyl, haloalkyl, alkoxy, haloalkoxy, alkenyloxy or haloalkenyloxy group, or a phenoxy or pyridyloxy group which group may be substituted by one or more of halogen atoms, and nitro, alkyl, haloalkyl and cyano groups; each Y independently represents a halogen atom or a nitro, cyano, alkyl or haloalkyl group; and p=0, 1, 2, 3 or 4.

2. A compound according to claim 1 wherein P is fluorine, m is 1, Q is fluorine and is bonded to the carbon atom at the other ortho position in the ring, the —COOR moiety is bonded to the carbon atom at the 2-position in the ring and R is a phenyl, q is 0, p is zero, and T is 2-chloro-4-trifluoromethylphenoxy.

3. A method for combatting unwanted insects and mites at a locus which comprises applying an effective amount of a compound of claim 1 to said locus.

4. An insecticidal and miticidal composition that comprises an effective amount of a compound of claim 1 together with an inert carrier.

* * * * *